(12) United States Patent
Lee et al.

(10) Patent No.: US 10,719,935 B2
(45) Date of Patent: Jul. 21, 2020

(54) IMAGE PROCESSING APPARATUS AND IMAGE PROCESSING METHOD THEREOF

(71) Applicant: Samsung Electronics Co., Ltd., Suwon-si, Gyeonggi-do (KR)

(72) Inventors: Jae-sung Lee, Seoul (KR); Gye-hyun Kim, Seoul (KR); Woo-hyun Nam, Seoul (KR); Yong-sup Park, Seoul (KR); Ji-hun Oh, Hwaseong-si (KR); Yun-sub Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 259 days.

(21) Appl. No.: 15/770,695

(22) PCT Filed: Nov. 14, 2016

(86) PCT No.: PCT/KR2016/013087
§ 371 (c)(1),
(2) Date: Apr. 24, 2018

(87) PCT Pub. No.: WO2017/099375
PCT Pub. Date: Jun. 15, 2017

(65) Prior Publication Data
US 2019/0066296 A1 Feb. 28, 2019

(30) Foreign Application Priority Data
Dec. 11, 2015 (KR) .................... 10-2015-0176983

(51) Int. Cl.
*G06T 7/30* (2017.01)
*G06T 7/10* (2017.01)
(Continued)

(52) U.S. Cl.
CPC ............ *G06T 7/0016* (2013.01); *A61B 5/055* (2013.01); *A61B 5/08* (2013.01); *A61B 6/03* (2013.01);
(Continued)

(58) Field of Classification Search
CPC ... G06T 7/10; G06T 7/11; G06T 7/174; G06T 7/30; G06T 7/38; G06T 7/97
See application file for complete search history.

(56) References Cited

U.S. PATENT DOCUMENTS

| | | | |
|---|---|---|---|
| 6,889,071 B2 | 5/2005 | Saranathan et al. | 600/413 |
| 7,116,810 B2 | 10/2006 | Miller et al. | 382/131 |

(Continued)

FOREIGN PATENT DOCUMENTS

| | | | | |
|---|---|---|---|---|
| JP | 4702971 B2 | 6/2011 | | A61B 6/03 |
| JP | 5067398 B2 | 11/2012 | | A61B 8/00 |

(Continued)

OTHER PUBLICATIONS

European Office Action dated May 6, 2019, issued in European Patent Application No. 16873241.0-1210.
(Continued)

*Primary Examiner* — Andrew W Johns
(74) *Attorney, Agent, or Firm* — Jefferson IP Law, LLP

(57) ABSTRACT

An image processing apparatus is disclosed. The image processing apparatus of the present invention comprises: an image receiving unit for receiving a first image and a second image of the same object taken at different times; a processor for obtaining transformation information by registering the first image on the basis of the second image, obtaining a first segment image corresponding to an area of the object from the first image, and generating a second segment image corresponding to an area of the object of the second image by transforming the obtained first segment image according
(Continued)

to the transformation information; and an output unit for outputting the second segment image.

15 Claims, 12 Drawing Sheets

(51) Int. Cl.
    *G06T 7/00*         (2017.01)
    *A61B 5/055*       (2006.01)
    *A61B 5/08*        (2006.01)
    *A61B 6/03*        (2006.01)
    *A61B 8/08*        (2006.01)
    *G06T 7/62*        (2017.01)
    *G06T 7/11*        (2017.01)
    *G06T 7/168*       (2017.01)
    *G06T 7/37*        (2017.01)
    *A61B 6/00*        (2006.01)

(52) U.S. Cl.
    CPC ............ *A61B 6/032* (2013.01); *A61B 6/5217* (2013.01); *A61B 8/08* (2013.01); *A61B 8/0858* (2013.01); *A61B 8/5223* (2013.01); *G06T 7/00* (2013.01); *G06T 7/10* (2017.01); *G06T 7/11* (2017.01); *G06T 7/168* (2017.01); *G06T 7/30* (2017.01); *G06T 7/37* (2017.01); *G06T 7/62* (2017.01); *G06T 2207/10081* (2013.01); *G06T 2207/10088* (2013.01); *G06T 2207/10104* (2013.01); *G06T 2207/10116* (2013.01); *G06T 2207/10132* (2013.01); *G06T 2207/30061* (2013.01)

(56) References Cited

U.S. PATENT DOCUMENTS

| | | | | |
|---|---|---|---|---|
| 7,835,555 | B2 | 11/2010 | Kiraly et al. | 382/128 |
| 8,094,896 | B2 | 1/2012 | Dutta et al. | 382/128 |
| 8,111,892 | B2 | 2/2012 | Hyun et al. | 382/131 |
| 9,262,685 | B2 | 2/2016 | Hwang et al. | G06K 9/4604 |
| 2004/0101182 | A1 | 5/2004 | Miller et al. | 382/131 |
| 2009/0257627 | A1 | 10/2009 | Nay et al. | 382/128 |
| 2014/0316247 | A1 | 10/2014 | Hwang et al. | A61B 5/0806 |
| 2015/0193943 | A1 | 7/2015 | Li | G06T 7/0093 |
| 2015/0289848 | A1 | 10/2015 | Hwang et al. | A61B 8/5261 |
| 2018/0268541 | A1* | 9/2018 | Kruecker et al. | G06T 7/0002 |

FOREIGN PATENT DOCUMENTS

| | | | | |
|---|---|---|---|---|
| JP | 2014-064835 A | 4/2014 | ............... | A61B 6/03 |
| KR | 10-1144579 B1 | 2/2011 | ............... | A61B 6/00 |
| KR | 10-1274530 B1 | 6/2013 | ............... | A61B 6/03 |
| KR | 10-2014-0100648 A | 8/2014 | ............... | A61B 6/03 |
| KR | 10-2014-0126815 A | 11/2014 | ............... | A61B 8/00 |
| KR | 10-2015-0118484 A | 10/2015 | ............... | G06T 7/00 |
| WO | 2015/101948 A2 | 7/2015 | | |

OTHER PUBLICATIONS

Ehrhardt et al.; Statistical Modeling of 4D Respiratory Lung Motion Using Diffeomorphic Image Registration; IEEE Transactions on Medical Imaging, vol. 30, No. 2; XP011330316; Feb. 2011.

Bottger et al.; Implementation and evaluation of a new workflow for registration and segmentation of pulmonary MRI data for regional lung perfusion assessment; IOP Publishing; Physics in Medicine and Biology; Phys. Med. Biol. 52; 1261-1275; XP020113220; Feb. 2, 2007.

Zheng et al.; Lung Nodule Growth Analysis from 3D CT Data with a Coupled Segmentation and Registration Framework; IEEE; XP031194639; 2007.

European Search Report dated Aug. 31, 2018; European Application No. 16873241.0-1210 / 3338629.

European Search Report dated Sep. 26, 2019; European Appln. No. 16 873 241.0-1210.

Craig J.Galban et al., Computed tomography-based biomarker provides unique signature for diagnosis of COPD phenotypes and disease progression, Nov. 2012, Nat. Med. 18(11), pp. 1711-1715.

Lo et al., Extraction of Airways from CT (EXACT'09), University of Copenhagen, 2012, IEEE Trans. on Medical Imaging, vol. 31, No. 11, pp. 2093-2107.

Hersh et al., 2013, Paired inspiratory-expiratory chest CT scans to assess for small airways disease in COPD, Respiratory Research.

Inoue et al., Robust Airway Extraction based on Machine Learning and Minimum Spanning Tree Fujifilm Corporation, 26-30 Nishiazabu, 2-Chome Minato-ku, Tokyo, Japan 106-8620, 2013, Proc. SPIE vol. 8670, Medical Imaging 2013: Computer-Aided Diagnosis.

Lutey, et al., Accurate Measurement of Small Airways on Low-Dose Thoracic CT Scans in Smokers, Chest Original Research, May 2013, pp. 1321-1329.

European Office Action dated Mar. 12, 2020, issued in European Patent Application No. 16873241.0 - 1210.

Korean Office Action dated Apr. 24, 2020, issued in Korean Patent Application No. 10-2015-0176983.

* cited by examiner

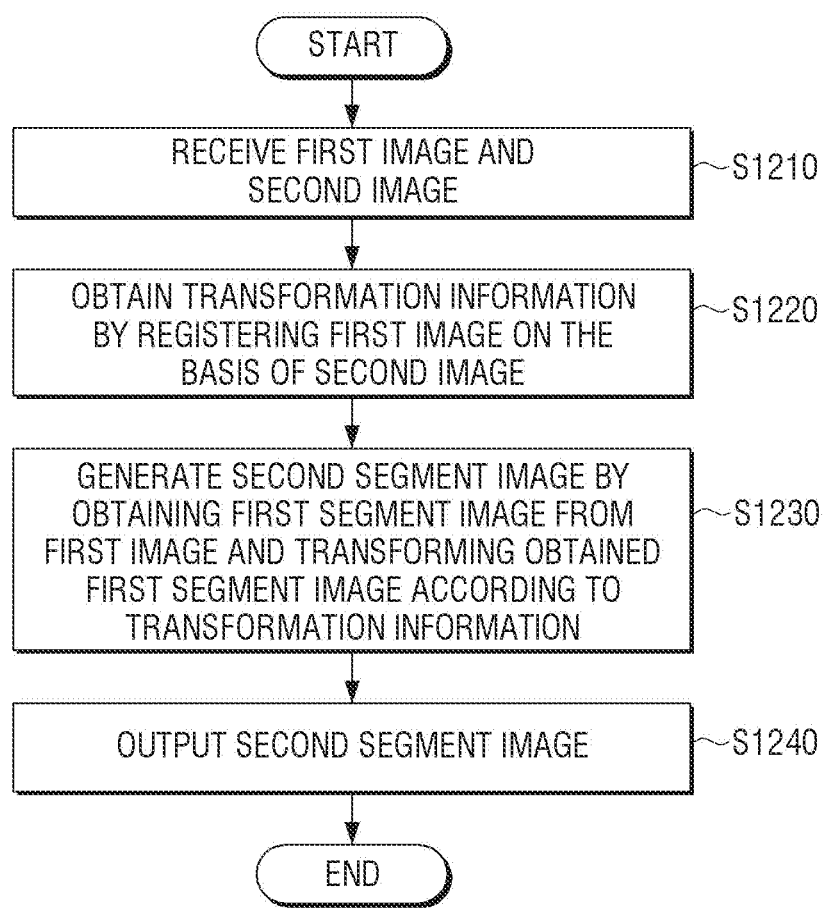

IMAGE PROCESSING APPARATUS AND IMAGE PROCESSING METHOD THEREOF

TECHNICAL FIELD

Apparatuses and methods consistent with example embodiments relate to an image processing apparatus and an image processing method thereof, and more particularly, to an image processing apparatus for segmenting, using an image which is generated by photographing the same object at different time points, an area of the object from the image, and an image processing method thereof.

DESCRIPTION OF RELATED ART

To photograph the internal structure of human body, various medical image apparatuses have been used. For example, a magnetic resonance imaging (MRI), a computed tomography (CT), an X-ray, a positron emission tomography (PET), an ultrasonic image apparatus and the like have been used.

It is necessary for the user of a medical image apparatus to diagnose a condition of a patient after comparing multiple medical images. For example, to diagnose bronchitis, a CT image may be used. In particular, observation of the degree of contraction and relaxation of the bronchi in the state of inhalation and exhalation can reveal the site of inflammation.

According to a recent research result, the bronchus should be shrunk at the time of exhalation, and the part where the contraction is not good should be suspected of diseases such as inflammation.

However, in the images taken at the time of inhalation, the bronchus is expanded, so it is easy to conduct analysis by the image processing. On the other hand, there is a problem that the bronchus becomes collapsed in the image taken at the time of exhalation and it is difficult to conduct analysis by the image processing.

DETAILED DESCRIPTION

Technical Problem

One or more example embodiments provide an image processing apparatus for segmenting, using an image generated by photographing the same object at different time points, an area of the object in the image, and an image processing method thereof.

Solution to Problem

According to an aspect of an example embodiment, there is provided an image processing apparatus, comprising: an image receiving unit for receiving a first image and a second image of the same object taken at different times; a processor for obtaining transformation information by registering the first image on the basis of the second image, obtaining a first segment image corresponding to an area of the object from the first image, generating a second segment image corresponding to an area of the object of the second image by transforming the obtained first segment image according to the transformation information, and an output unit for outputting the second segment image.

The processor may control the output unit to output the first segment image obtained from the first image together with the second segment image.

The processor may control the output unit to output a comparison result between the first segment image obtained from the first image and the second segment image.

The object may be a bronchus. The first image may be an image taken during inhalation. The second image may be an image taken during exhalation. The processor may compare the first segment image and the second segment image and control the output unit to output information relating to a change of the bronchus during inhalation and exhalation.

The information relating to the change of the bronchus may be information relating to a change of at least one of a thickness of a bronchus wall, a cross-sectional area of a bronchus wall, a diameter of a bronchus, a cross-sectional area of a bronchus, a ratio of a diameter of a bronchus to a thickness of a bronchus wall, and a ratio of a cross-sectional area of a bronchus to a cross-sectional area of a bronchus wall.

The processor may, in response to the first image including a plurality of images of the first image taken at different times, obtain a plurality of first segment image from the plurality of images, generate a plurality of transformation images by transforming the plurality of first segment images according to a plurality of transformation information acquired in a registration process of the plurality of images, and generate the second segment images by combining the plurality of transformation images.

At least one of the first image and the second image may be an image which is acquired through a computed tomography (CT) apparatus, a magnetic resonance imaging (MRI) apparatus, an ultrasound imaging apparatus, a positron emission tomography (PET) apparatus, or an X-ray apparatus.

The processor may obtain the second image from an image pre-stored in the image processing apparatus and receive the first image from an external server.

According to an aspect of an example embodiment, there is provided an image processing method of an image processing apparatus, the method comprising: receiving a first image and a second image of the same object taken at different times; obtaining transformation information by matching the first image on the basis of the second image; and generating a second segment image corresponding to an area of the object of the second image by obtaining a first segment image corresponding to an area of the object from the first image and transforming the obtained first segment image according to the transformation information.

The outputting may include the first segment image obtained from the first image together with the second segment image.

The outputting may include outputting a comparison result between the first segment image obtained from the first image and the second segment image.

The object may be a bronchus. The first image may be an image taken during inhalation. The second image may be an image taken during exhalation. The outputting may include comparing the first segment image and the second segment image and outputting information relating to a change of the bronchus during inhalation and exhalation.

The information relating to the change of the bronchus may be information relating to a change of at least one of a thickness of a bronchus wall, a cross-sectional area of a bronchus wall, a diameter of a bronchus, a cross-sectional area of a bronchus, a ratio of a diameter of a bronchus to a thickness of a bronchus wall, and a ratio of a cross-sectional area of a bronchus to a cross-sectional area of a bronchus wall.

The generating the second segment image may include, in response to the first image including a plurality of images of the first image taken at different times, obtaining a plurality of first segment image from the plurality of images, generating a plurality of transformation images by transforming the plurality of first segment images according to a plurality of transformation information acquired in a registration process of the plurality of images, and generating the second segment images by combining the plurality of transformation images At least one of the first image and the second image may be an image which is acquired through a computed tomography (CT) apparatus, a magnetic resonance imaging (MRI) apparatus, an ultrasound imaging apparatus, a positron emission tomography (PET) apparatus, or an X-ray apparatus.

The receiving may include obtaining the second segment image from an image pre-stored in the image processing apparatus and receiving the first image from an external server.

According to an aspect of an example embodiment, there is provided a computer-readable recording medium of which stored a program for executing an image processing method of an image processing apparatus, the image processing method comprising: receiving a first image and a second image of the same object taken at different times; obtaining transformation information by matching the first image on the basis of the second image; generating a second segment image corresponding to an area of the object by obtaining a first object image corresponding to the object from the first image and transforming the obtained first object image according to the transformation information; and outputting the second object image.

BRIEF DESCRIPTION OF DRAWINGS

FIG. 12 is a flowchart illustrating an image processing method of an image processing apparatus, according to an example embodiment.

PREFERRED EMBODIMENTS FOR CARRYING OUT THE INVENTION

Hereinafter, the present disclosure will be described in detail with reference to the accompanying drawings. Also, well-known functions or constructions are not described in detail since they would obscure the disclosure with unnecessary detail. Among the terms used herein, those that are defined in the dictionaries may be interpreted based on the same or similar definitions that can be understood in the associated technical context, and unless specifically defined otherwise, these are not interpreted as ideal or unnecessarily formal ways. Therefore, the terms used in the exemplary embodiments should be defined based on the meaning thereof and the descriptions of the present disclosure, rather than based on their names only.

The term "image" as referred to herein may refer to multi-dimensional data including discrete image elements (e.g., pixels in a two-dimensional image and voxels in a three-dimensional image).

The term "object" as referred to herein may refer to human, animal, or a part of human or animal. For example, a subject may include lung, airway, bronchus, liver, heart, uterus, brain, breast, abdomen, blood vessel and the like.

Figure 1:
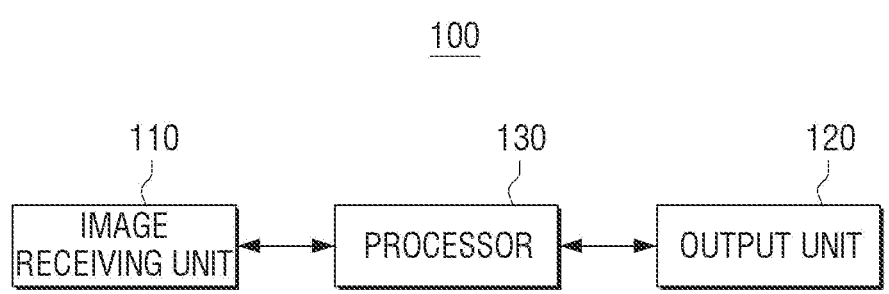
FIG. 1 is a block diagram illustrating an image processing apparatus, according to an example embodiment.

FIG. 1 is a block diagram illustrating a configuration of an image processing apparatus 100, according to an example embodiment.

Referring to FIG. 1, the image processing apparatus 100 may include an image receiving unit 110, an output unit 120, and a processor 130.

The image receiving unit 110 may receive images through various sources. For example, the image receiving unit 110 may receive various images from a storage medium within the image processing apparatus 100, an external storage medium and an external server according to various communication interfaces.

The image receiving unit 110 may perform communication with various external sources according to various communication protocols. In more detail, various communication interfaces, such as IEEE, Wi-Fi, Bluetooth, 3G, 4G, near field communication (NFC), USB (universal serial bus), HDMI (high definition multimedia interface) and the like, may be used. The image receiving unit 110 may include a WiFi chip, a Bluetooth® chip, an NFC chip, and a wireless communication chip.

In particular, the image receiving unit 110 may receive an image from various medical apparatuses. For example, an image which is photographed through a computed tomography (CT) apparatus, a magnetic resonance imaging (MRI) apparatus, an ultrasound imaging apparatus, a positron emission tomography (PET) apparatus, a single photon emission computed tomography (SPECT) apparatus, an X-ray apparatus, and the like, may be received. Alternatively, the image processing apparatus 100 itself may be a medical apparatus as described above, and in this case, the image receiving unit 100 may receive an image from an internal storage medium.

The images received through the image receiving unit 110 may be images which are generated by photographing the same object at different times.

The output unit 120 is a configuration which is capable of outputting various information in various ways.

For example, the output unit 120 may be implemented to transmit various information to an external apparatus. In this regard, the external apparatus may be an apparatus, such as a smartphone, a tablet PC, a desktop PC, a monitor, a projector, and the like, which is capable of displaying a received image.

The output unit 120 may transmit information to an external apparatus in various communication methods, such as IEEE, Wi-Fi, Bluetooth, 3G, 4G, near field communication (NFC), USB (universal serial bus), HDMI (high definition multimedia interface) and the like. In a case in which the output unit 120 and the image receiving unit 110 have a function of communicating with an external apparatus in common, the two configurations may be implemented as one configuration instead of two separate configurations.

According to another example embodiment, the output unit 120 may be implemented as a display which is capable of visually outputting information. For example, the output unit 120 may be, for example, implemented as a liquid crystal display (LCD), a cathode-ray tube (CRT), a plasma display panel (PDP), an organic light emitting diode (OLED) display, a transparent OLED (TOLED) display, or the like.

In particular, the output unit 120 may output an image which is processed by the processor 130. In addition, the output unit 120 may output comparison results between images under the control of the processor 130. In this regard, the comparison results may be output in various formats, such as image, text, and the like.

The processor 130 may control the overall operation of the image processing apparatus 100.

The processor 130 may include a RAM, a ROM, a main CPU, various interfaces, and a bus. The RAM, the ROM, the main CPU, the various interfaces, and the like may be interconnected with each other via a bus, and transmit or receive various data, signals, and the like.

The processor 130 may perform an image registration processing. The image registration is a process of acquiring matching information between images obtained by photographing the same object at different times or viewpoints.

In more detail, in a case in which the same object is photographed at different times or viewpoints, images are acquired in different coordinate systems. The image registration is a processing scheme to modify these different images and represent them in one coordinate system. Through the image registration, matching information of images acquired at different measurement time points or through different methods may be obtained.

The image registration algorithm may be divided into an intensity-based method and a feature-based method.

The image registration is a process of matching an image with a fixed image. The fixed image may be called a reference image or an original image, and the image to be aligned with the fixed image may be called a moving image. In the description relating to image registration in the present disclosure, it is defined that the term "first image" refers to an moving image and the term "second image" refers to a reference image.

The image registration includes a process of spatially modifying a moving image and matching it with a reference image. The intensity-based method is a method of comparing a shape of intensity of an image. The feature-based method is a method of searching for a dot, a line, an edge and the like in an image and matching them with each other. The intensity-based method compares images in their entirety and registers them, whereas the feature-based method searches for multiple features in images and compares them. If a corresponding relationship between some numbers of feature points in two images is identified, a transformation relationship between the two images can be determined and thus, a corresponding relationship of the other points in the images may be calculated.

Meanwhile, the image registration includes a homogeneous registration method and an in-homogeneous registration method. The homogeneous registration is a method of matching a moving image with a reference image while maintaining an image characteristic (or shape) of the moving image. The homogeneous registration is a method of matching a moving image with a reference image while maintaining an image characteristic (or shape) of the moving image.

The image registration algorithm may be classified according to a transformation relationship between a reference image and a moving image. Broadly, as a second scope, the image registration algorithm may be classified into a linear transformation including translation, rotation, scaling, affine transform, and the like. However, the linear transformation cannot explain a geometrical transformation between images. As a second scope, the image registration algorithm includes elastic transformation, or nonrigid transformation. A transformation model may, for example, include rigid transformation, affine transformation, thin-plate-spline free form deformation (FFD), B-spline FFD, an elastic model, and the like.

The processor 130, from among a first image and second image which are generated by photographing the same object at different times, performs an image registration to register the first image based on the second image.

In an example embodiment, the image registration is performed through a process of acquiring $p_{final}$ with the similarity measure (S) function value expressed in the mathematical equation 1 as shown below as the maximum, or with the cost function (C) value expressed in the mathematical equation 2 as the minimum. P refers to a parameter set of transformation model. In the equations below, $I_f$ refers to a fixed image and $I_m$ refers to a moving image.

$$p_{final} = \operatorname*{argmax}_{p} S(I_f, I_m; p) \quad \text{Equation 1}$$

$$p_{final} = \operatorname*{argmin}_{p} C(I_f, I_m; p) \quad \text{Equation 2}$$

Meanwhile, $p_{final}$ which is acquired through the image registration may be understood to have the same meaning as the term "transformation information" as referred to in the present disclosure.

Figure 2:
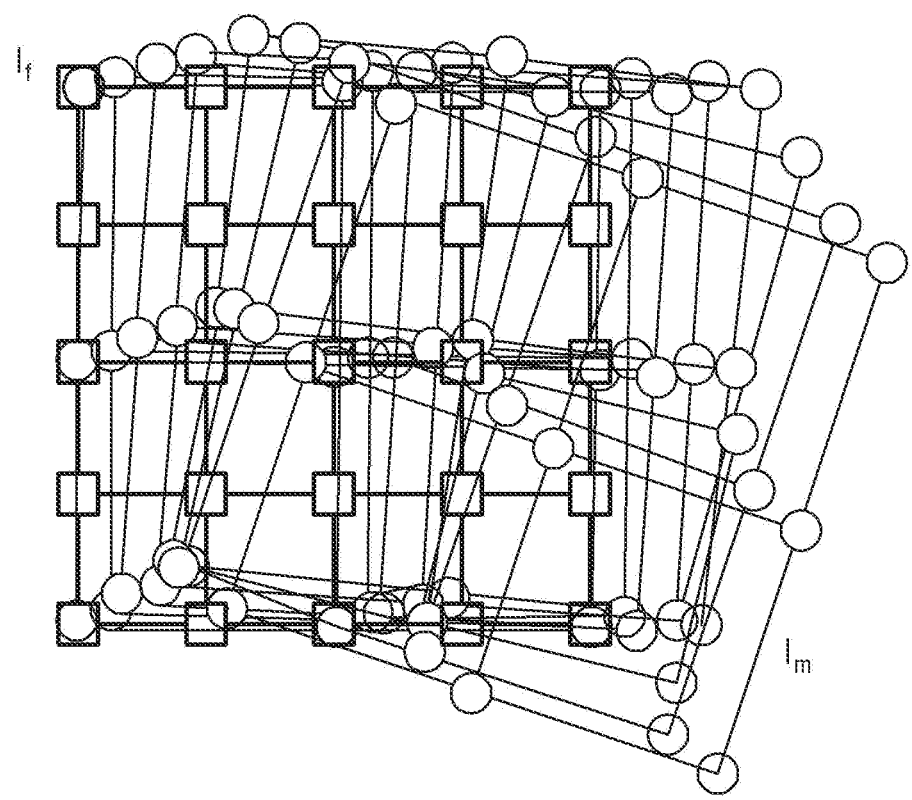
FIG. 2 is a diagram illustrating an image registration processing of an image processing apparatus, according to an example embodiment.

FIG. 2 is a diagram schematically illustrating an image registration. Referring to FIG. 2, a rectangle refers to pixels of a reference image ($I_f$), and a circle refers to pixels of a moving image ($I_m$). As illustrated in FIG. 2, the image registration includes a series of processes to gradually modify a moving image ($I_m$) to be similar to a reference image ($I_f$).

Figure 3:
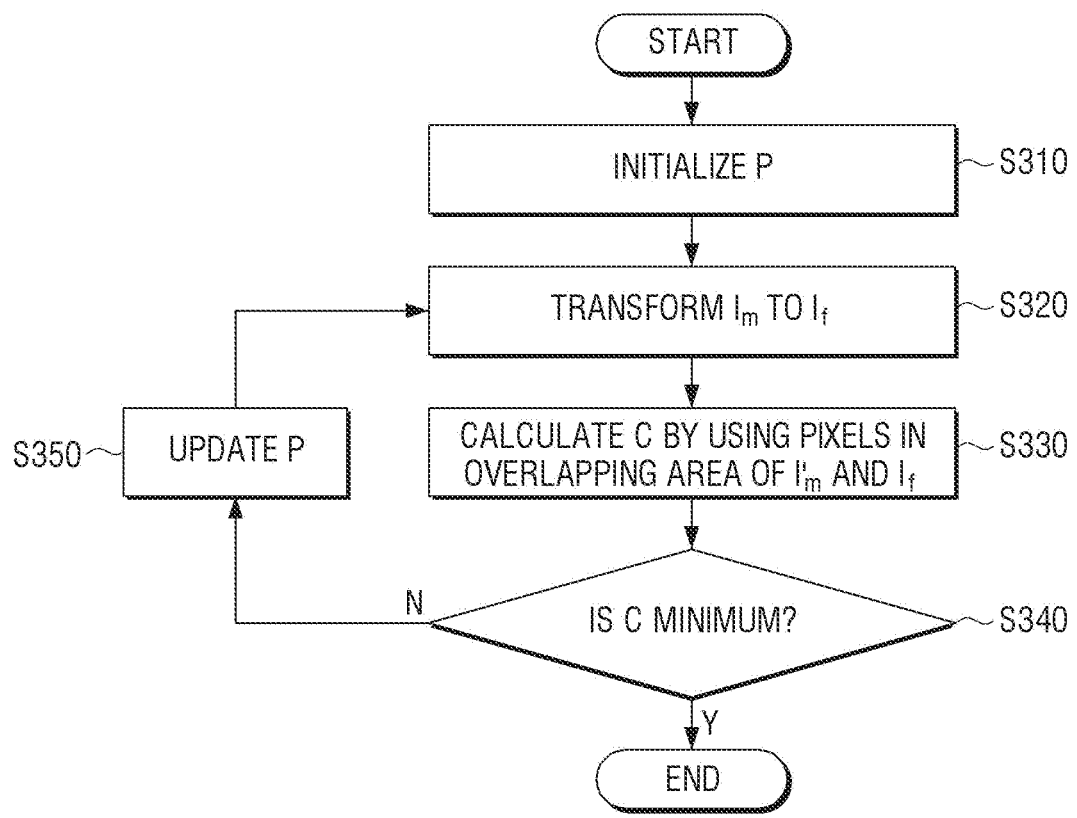
FIG. 3 is a flowchart illustrating an example image registration algorithm.

FIG. 3 is a flowchart illustrating an example image merging algorithm obtaining $p_{final}$ described above.

Referring to FIG. 3, first, the processor 130 is configured to initialize p which is a parameter set of transformation model, at operation S310. In addition, the processor performs transformation with respect to a moving image ($I_m$) (or a first image) based on a reference image ($I_f$) (or a second image), at operation S320. In this regard, a rigid global model, a non-rigid global model, a rigid local model, a non-rigid local model, and the like may be used for the transformation.

In addition, a cost function (C) is calculated using pixels in an overlapping area of the transformed first image ($I'_m$) and the second image ($I_f$), at operation S330. In this regard, the cost function may be a function including a regularization metric and similarity (or dis-similarity) measure.

The regularization metric may include volume regularization, diffusion regularization, curvature regularization, local rigidity constraint, and the like. In addition, the similarity (or dis-similarity) measure may include mutual information (MI), normalized mutual information (NMI), gradient-magnitude, gradient-orientation, sum of squared difference (SSD), normalized gradient-vector flow (NGF), gradient NMI (GNMI), and the like.

In addition, it is identified whether the calculated cost function (C) is a minimum value, at operation S340. In this regard, an optimization algorithm may be used.

When the calculated cost function (C) is a minimum value, the p at that time is acquired as $p_{final}$.

If the calculated cost function (C) is not a minimum value, the p is updated at operation S350, and the step S320 is proceeded again.

In the image registration process as described above, the transformation model and the regularization metric of the cost function are designed to thereby induce a result of homogeneous registration or a result of in-homogeneous registration differently.

Meanwhile, the processor 130 may perform an image segmentation processing and obtain a segment image corresponding to an area of an object in the image. The image registration and the image segmentation are image processing which are carried out in parallel with each other.

For example, the image segmentation may be performed based on a difference of contrast. In this case, a threshold method, a boundary-based method, a region-based method, a hybrid method in which the boundary-based method and the region-based method are interchangeably used, and the like may be used. From among them, a region growing algorithm in the region-based method is most commonly used.

Figure 4:
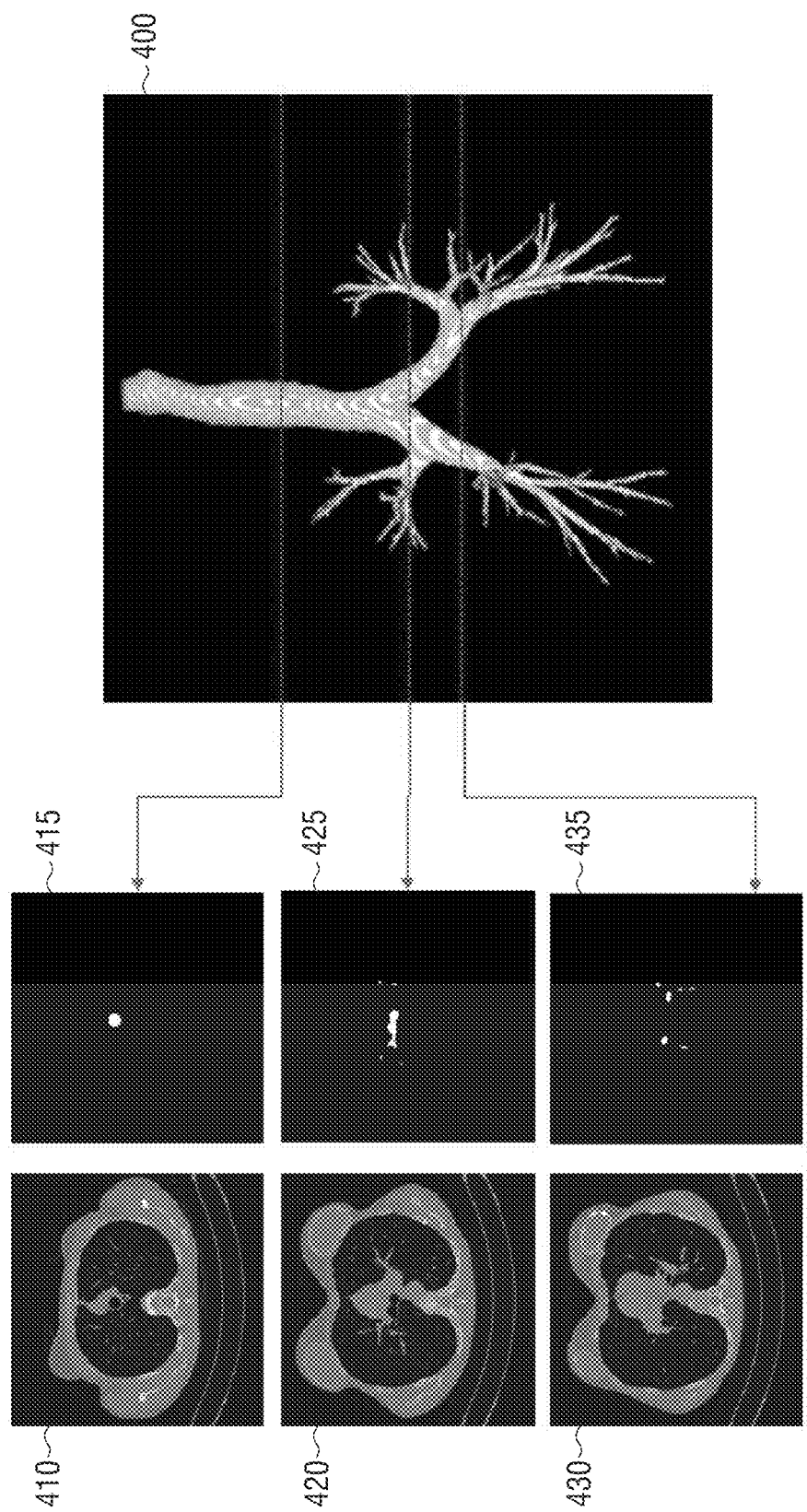
FIG. 4 is a diagram illustrating an image segmentation processing of an image processing apparatus, according to an example embodiment.

FIG. 4 is a diagram illustrating an intensity-based region growing algorithm which is an example of an image segmentation method.

Referring to FIG. 4, the images indicated by 410, 420 and 430 are CT tomographic images which are generated by photographing a bronchus which is an object. The processor 130 may identify an area of a bronchus, which is an object, from each of the CT tomographic images 410, 420 and 430. In more detail, the area of the bronchus includes air and thus has low density, and thus is darker than a peripheral area. Accordingly, the processor 130 extracts a seed point based on this difference of contrast and adds pixels that have a low image value. As a result of this process, segment images 415, 425 and 435 which are generated by segmenting the area of the bronchus may be acquired from each of the CT tomographic images 410, 420 and 430.

In addition, the processor 130 may combine the segment images 415, 425 and 435 and generate an image 400 generated by shaping the object three-dimensionally.

Figure 5:
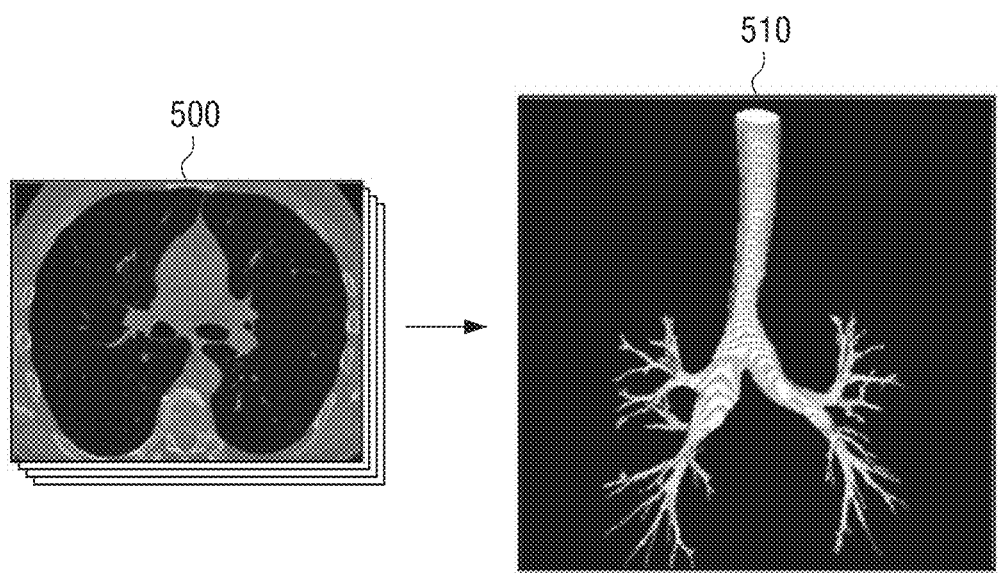
FIG. 5 is a diagram illustrating an example in which a bronchus area is segmented from an image photographed at the time of inhalation.

In a case in which an object is a bronchus, during inhalation, the bronchus is sufficiently filled with air and thus, a difference of contrast between the bronchus and the peripheral area is clear, rendering good image segmentation performance. FIG. 5 illustrates a segment image 500 of a bronchus during inhalation which is generated by obtaining the bronchus, which is an object, from a CT image 500 photographed during inhalation.

Figure 6:
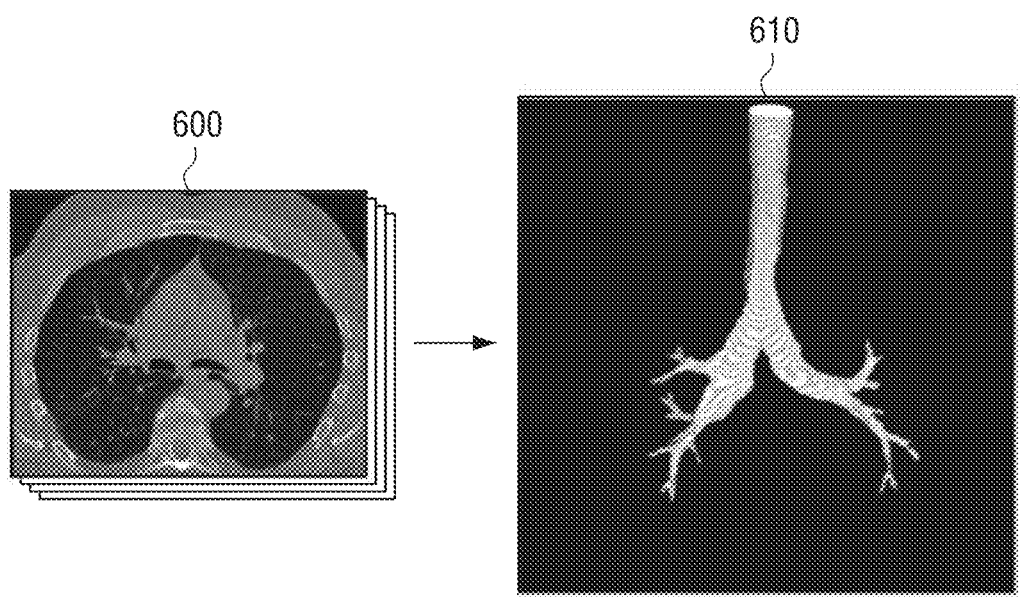
FIG. 6 is a diagram illustrating an example in which a bronchus area is segmented from an image photographed at the time of exhalation.

On the other hand, during exhalation, air is not sufficient in the bronchus and thus, a performance of the image segmentation is deteriorated. FIG. 6 illustrates a segment image 610 of a bronchus during exhalation which is generated by obtaining the bronchus, which is an object, from a CT image 600 photographed during exhalation. Compared with the segment image 510 of the bronchus during inhalation illustrated in FIG. 5, it can be understood that the bronchus in the segment image 610 of the bronchus during exhalation is displayed significantly smaller.

To resolve the problem that the segmentation performance during exhalation is deteriorated, the processor 130 may segment an object (bronchus) in the second image with enhanced segmentation performance by using transformation information acquired from the above-described registration process, that is, a process of registering the first image (e.g., image during inhalation) based on the second image (e.g., image during exhalation). This will be described in more detail below with reference to FIG. 7.

Figure 7:
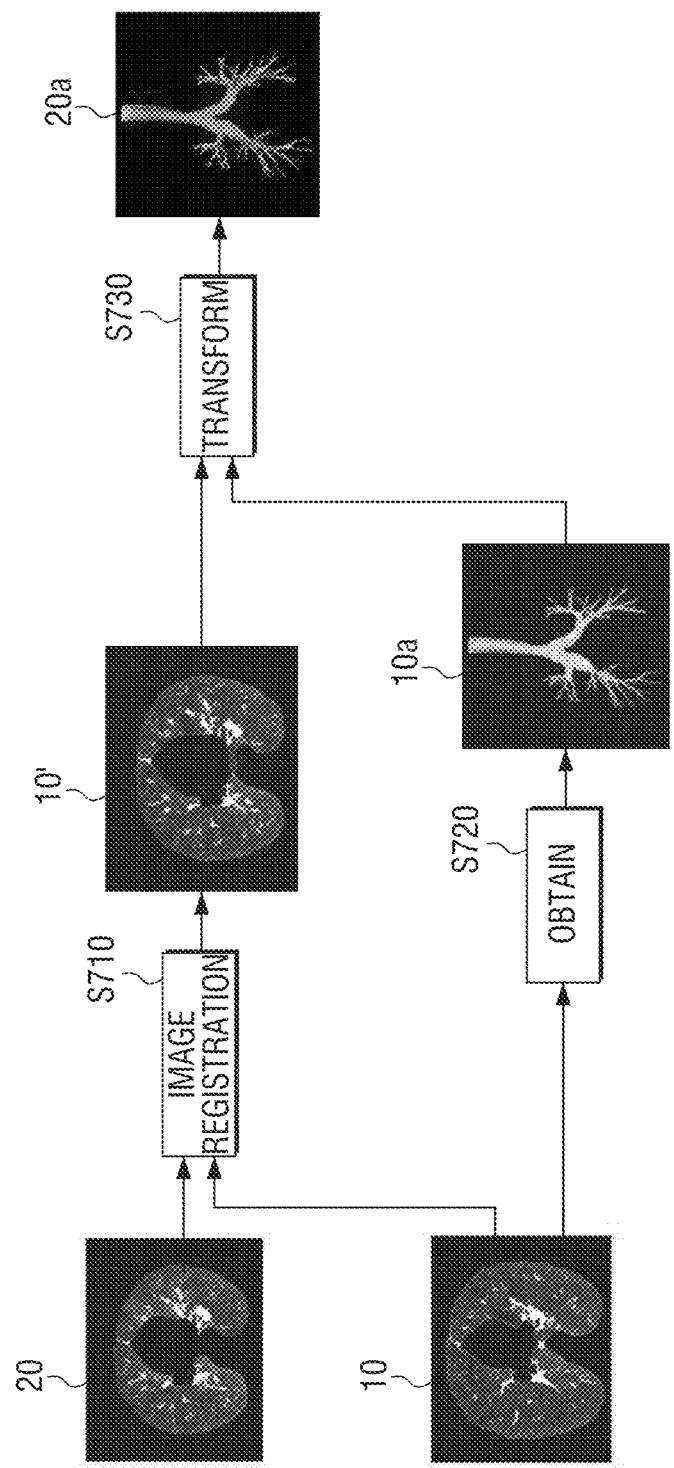
FIG. 7 is a diagram illustrating an image transformation method of an image processing apparatus, according to an example embodiment.

FIG. 7 is a diagram illustrating an image transformation method, according to an example embodiment. Referring to FIG. 7, an image during inhalation corresponds to a first image, and an image during exhalation corresponds to a second image. In addition, an object is a bronchus. In other words, the first image and the second image correspond to images which are generated by photographing the same object at different times.

Referring to FIG. 7, the processor 130 registers a first image 10 based on a second image 20, at operation S710. In addition, the processor 130 obtains a first segment image 10a corresponding to an area of an object from the first image 10 according to an image segmentation algorithm at operation S720.

In addition, the processor 130 transforms, at operation S730, the first segment image 10a according to transformation information acquired in the image registration process (operation S710) and generates a second segment image 20a.

In other words, the transformation information acquired by registering the first image based on the second image is matching information between the first image and the second image. Thus, the second segment image 20a which is generated by transforming the first segment image 10a according to the transformation information corresponds to an area of an object of the second image 20.

According to an example embodiment, by using the first image 10 during inhalation from which a bronchus can be obtained with good segmentation performance, an area of bronchus in the second image 20 during exhalation where it is difficult to obtain the bronchus with good segmentation performance can be obtained with good segmentation performance.

In the above example embodiment, images that are generated during inhalation and exhalation are used, but the example is not limited thereto. To obtain an area of an object from a particular image with enhanced segmentation performance, all examples of using an image photographed at a different time point from the particular image are to be included in the present disclosure. For example, to obtain an area of bronchus from an image photographed today, an image photographed a month ago may be used.

In the above example embodiment, a first image is photographed at a time point which is different from a time point at which a second image is photographed. However, the example is not limited thereto, and the first image may include a plurality of images which are photographed at different time points.

In more detail, in a case in which the first image includes a plurality of images which are generated by photographing the same subject at different time points, the processor 130 may obtain a plurality of first segment images from the plurality of images. In addition, the processor 130 may register each of the plurality of images based on the second image. In addition, by using a plurality of transformation information acquired in this registration process, the processor 130 may transform each of the plurality of first segment images and generate a plurality of transformation images. In addition, the processor 130 may generate a second segment image by combining a plurality of transformation images.

As described above, if an image photographed at more different time points is used, a second segment image corresponding to an area of an object may be acquired from the second image with a better segmentation performance.

The present example embodiment will be described in greater detail below with reference to FIGS. 8 and 9.

Figure 8:
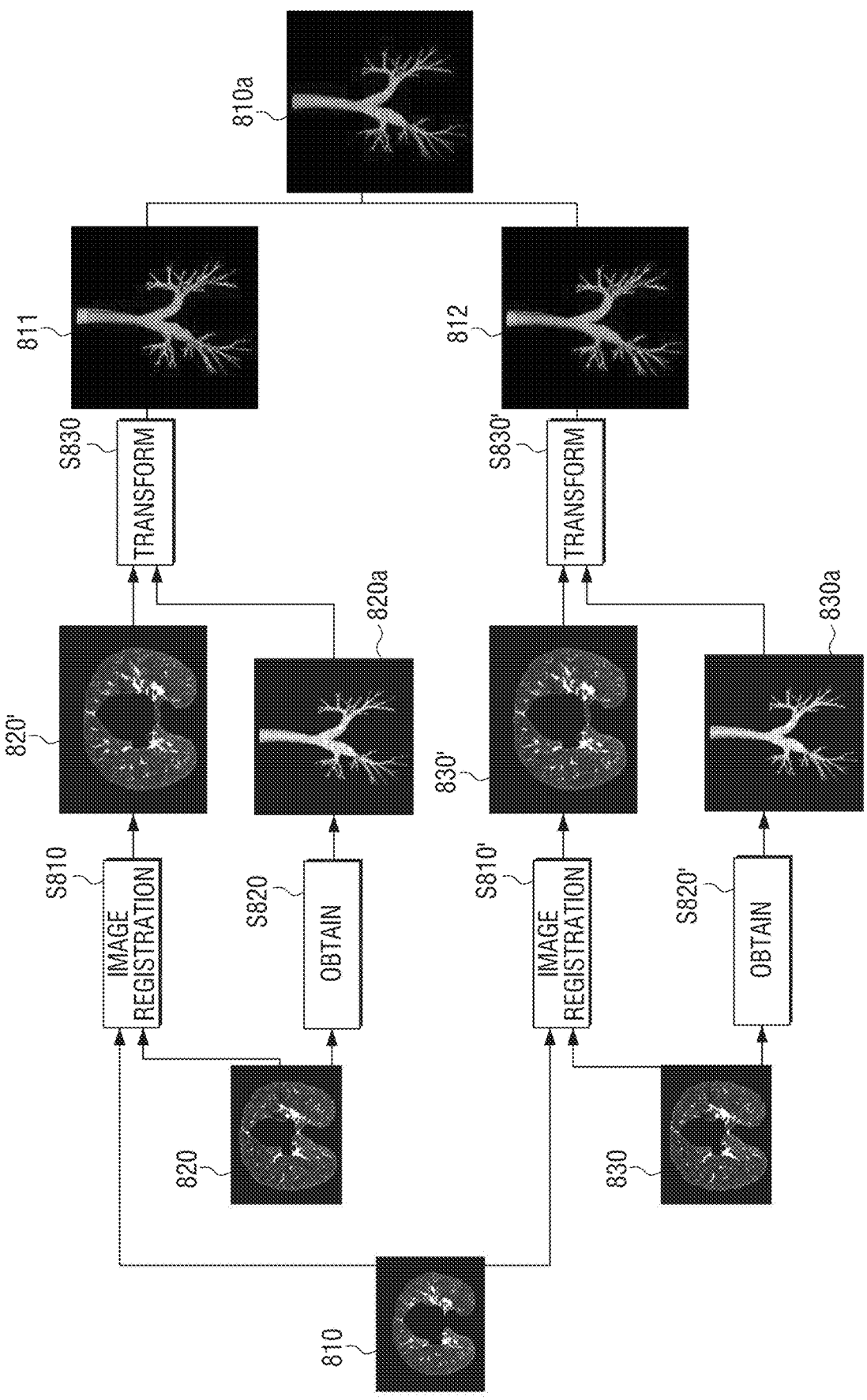
FIG. 8 is a diagram illustrating an image transformation method of an image processing apparatus, according to another example embodiment.

FIG. 8 is a diagram illustrating a process of acquiring a current segment image 810*a* corresponding to an area of an object from a current image 810 by using an image 820 at a previous first time point and an image 830 at a previous second time point.

Referring to FIG. 8, the processor 130 registers the image 820 at the previous first point based on the current image 810, at operation S810. In addition, the processor 130 registers the image 830 at the previous second point based on the current image 810, at operation S810'.

In addition, the processor 130 obtains a first segment image 820*a* at a previous first point corresponding to an area of an object from the image 820 at the previous first point according to an image segmentation algorithm, at operation S820. In addition, the processor 130 obtains a segment image 830*a* at the previous second time point corresponding to an area of an object from the image 830 at the previous second time point according to the image segmentation algorithm, at operation S820'.

In addition, the processor 130 transforms, at operation S830, the segment image 820*a* at the previous first point according to transformation information acquired in the image registration process (operation S810) with respect to the image at the previous first time point and generates a first transformation image 811. In addition, the processor 130 transforms, at operation S830', the segment image 830*a* at the previous second point according to transformation information acquired in the image registration process (operation S810') with respect to the image at the previous second time point and generates a second transformation image 812.

In addition, the processor 130 combines the first transformation image 810 with the second transformation image 812 and generates a current segment image 810*a*. The way how the first transformation image 811 and the second transformation image 812 may be carried out using the method illustrated in FIG. 9 which will be described below with reference to FIG. 9.

Figure 9:
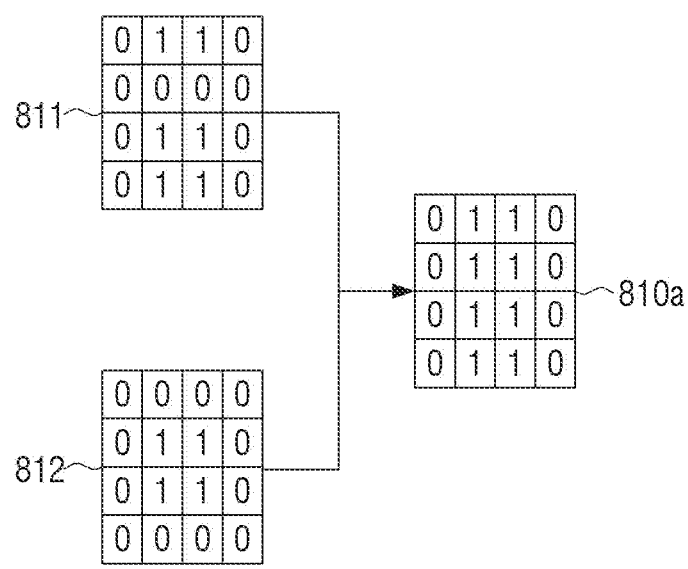
FIG. 9 is a diagram illustrating a combination of transformation images, according to an example embodiment.

Referring to FIG. 9, the first transformation image 811 and the second transformation image 812 are a binary image including 0s and 1s. The processor 130 may add image value of each of corresponding pixels of the first transformation image 811 and the second transformation image 812, correct pixels having a value greater than or equal to 2 to 1, and generate a current segment image 810*a*.

In the above example embodiment, images photographed at the previous first time point and the previous second time point which are different from each other are used. However, the example is not limited thereto, and it is possible to use images which are photographed at more than two time points.

Meanwhile, the processor 130 may provide a second segment image corresponding to an area of an object of the second image acquired as in the above examples to the user via the output unit 120.

In this regard, the processor 130 may control the output unit 120 to output a first segment image obtained from the first image together with the second segment image. For example, in FIG. 5, the first segment image 10*a* and the second segment image 20*a* may be output together via the output unit 120. Accordingly, the user can compare an object in the first image with an object in the second image at a glance.

According to another example embodiment, the processor 130 may control the output unit to output a comparison result of the first segment image obtained from the first image and the second segment image. In this regard, the comparison result may be information which shows a change in the shape of an object in the two images.

For example, in a case in which an object is a bronchus, the first image is an image photographed during inhalation, and the second image is an image photographed during exhalation, the processor 130 may compare a first segment image generated by obtaining an area of the object from the first image with a second segment image corresponding to an area of an object of the second image, and control the output unit 120 to output information relating to a change of bronchus during inhalation and exhalation. Accordingly, a user, for example, a doctor, can identify a change of bronchus during inhalation and exhalation at a glance.

The information relating to a change of bronchus may be information relating to a change of at least one from among a thickness of a bronchus wall, a cross-sectional area of a bronchus wall, a diameter of a bronchus, a cross-sectional area of a bronchus, a ratio of a diameter of bronchus to a thickness of a bronchus wall, and a ratio of a cross-sectional area of bronchus to a cross-sectional area of a bronchus wall.

Figure 10:
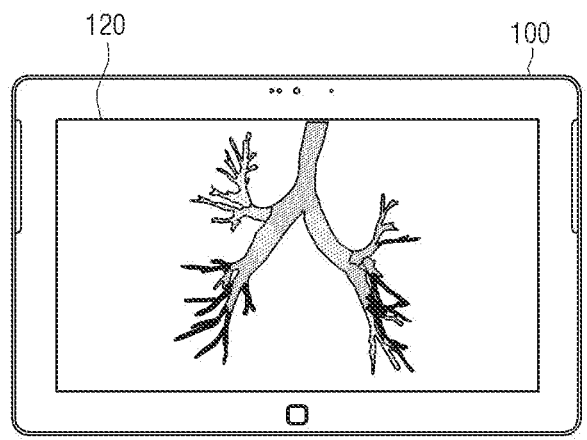
FIG. 10 is a diagram illustrating an information providing method of an image processing apparatus, according to an example embodiment.

Meanwhile, the information relating to a change of bronchus may be represented with a plurality of different colors. FIG. 10 illustrates an example of an information output result relating to a change of bronchus.

FIG. 10 illustrates a case in which an image processing apparatus 100 is implemented as a portable terminal. In this regard, the output unit 120 corresponds to a display included in the image processing apparatus 100.

Referring to FIG. 10, a processor 130 of the image processing apparatus 100 may compare diameters of a bronchus during inhalation and exhalation, and as a ratio of the diameter of bronchus during inhalation to the diameter of bronchus during exhalation gets higher, that is, as contraction is carried out more smoothly during exhalation, control the output unit 120 to output the portion to be lighter. To prepare for the above, a portion in which contraction is not smoothly carried out may be displayed to be darker. In other words, a terminal end portion of the bronchus which is determined to be not smoothly contracted may be displayed to be relatively darker as illustrated in FIG. 10.

Alternatively, the portion may be expressed in a different color. For example, the processor 130 of the image processing apparatus 100 may compare diameters of a bronchus during inhalation and exhalation, and as a ratio of the diameter of bronchus during inhalation to the diameter of bronchus during exhalation gets higher, that is, as contraction is carried out more smoothly during exhalation, control the output unit 120 to output the portion in a color having a short wavelength. Accordingly, a portion in which contraction is not smoothly carried out may be expressed in red color.

The information relating to a change of an object within an image may be expressed with a contrast, a color, and the like as mentioned above, but is not limited thereto, and may be expressed in a different way. For example, the information relating to a change of an object within an image may be expressed with a text. In this case, a text such as "inflammation is suspected" may be displayed in the output unit to indicate the portion in which contraction is not smoothly carried out during exhalation. Alternatively, it is possible that a change rate is expressed in numbers.

Figure 11:
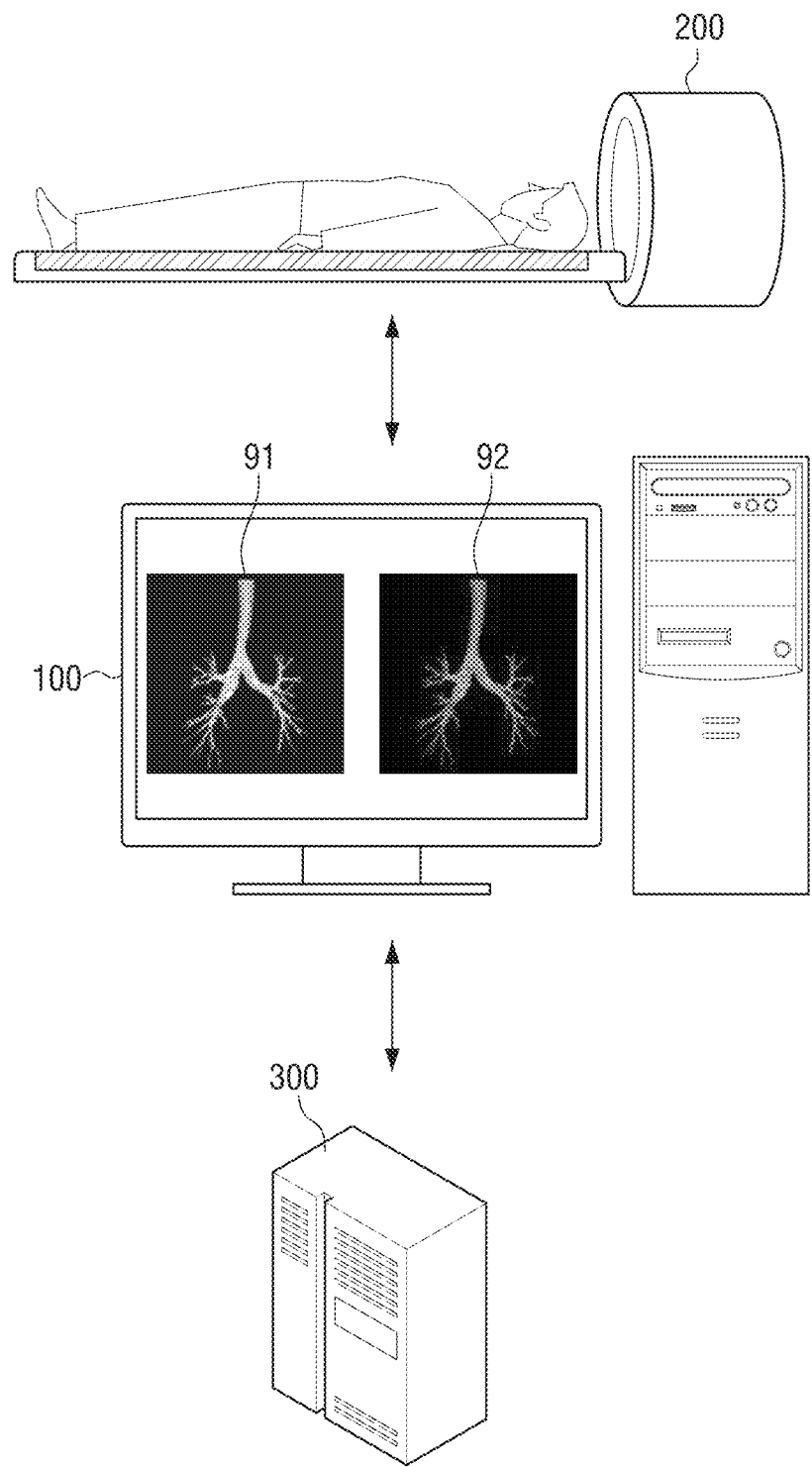
FIG. 11 is a diagram illustrating an image processing system, according to an example embodiment.

FIG. 11 is a diagram illustrating an image processing system, according to an example embodiment.

The image processing system may include an image processing apparatus 100, a medical apparatus 200, and a server 300.

The medical apparatus 200 may be a computed tomography (CT) apparatus, a magnetic resonance imaging (MRI) apparatus, an ultrasound imaging apparatus, a positron emission tomography (PET) apparatus, a single photon emission computed tomography (SPECT) apparatus, an X-ray apparatus, and the like.

The medical apparatus 200 may communicate with the image processing apparatus 100. In more detail, a photographing command may be received from the image processing apparatus 100, and an image generated by photographing an object according to the photographing command may be transmitted to the image processing apparatus 100.

In addition, the medical apparatus 200 may transmit an image to an external server. Accordingly, although not illustrated, the medical apparatus 200 may communicate with the server 300 as well and transmit the image to the server 300.

The server 300 is an apparatus which is capable of storing various medical information. In more detail, the server 300 is an apparatus which is capable of computerizing all information of a patient, such as personal data previously recorded in a paper chart, medical history, health condition, physical examination, hospitalization and discharge record, and the like, and receive, manage and store the information. For example, the server 300 may be an apparatus which performs an electronic medical record (EMR) function or an electronic health record (EHR) function.

Alternatively, the server 300 may be a picture archiving communication system (PACS). The PACS refers to a system which is capable of storing medical images generated by photographing a patient by using various medical image equipment and providing an image search service.

The server 300 may transmit past images of the patient to the image processing apparatus 100.

The image processing apparatus may receive a first image and second image which are generated by photographing the same object at different times as described above. In this regard, the first image is a current image of a patient which is received from the medical apparatus 200, and the second image is a past image of the same patient which is received from the server 300.

In addition, the image processing apparatus 100 may register the first image based on the second image and acquire transformation information as described above.

In addition, the image processing apparatus 100 may obtain a first segment image corresponding to an area of an object from the first image, transform the obtained a first segment image according to the acquired transformation information, and generate a second segment image corresponding to an area of an object of the second image.

Referring to FIG. 11, the image processing apparatus 100 may output a first segment image 91 obtained from the first image together with a second segment image corresponding to an area of an object of the second image. In other words, an image generated by obtaining an object from a current image of a patient is together output with an image generated by obtaining an object from a past image of the patient, and thereby a user, that is, a doctor, can easily compare a past condition and current condition of the patient.

According to the various example embodiments described above, when an object to be analyzed in any of a plurality of images is to be obtained, an object may be obtained with better segmentation performance using an image generated by photographing the object at another time.

Meanwhile, in the above example embodiment, a plurality of images photographed at different times are described. However, the example is not limited thereto, and it is possible to use a plurality of images photographed from different directions at the same time point or a plurality of images photographed by different photographing apparatuses at the same time point.

Various exemplary embodiments described above may be embodied in a recording medium that may be read by a computer or a similar apparatus to the computer by using software, hardware, or a combination thereof. According to the hardware embodiment, exemplary embodiments that are described in the present disclosure may be embodied by using at least one selected from Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, electrical units for performing other functions. In some cases, embodiments described herein may be implemented by processor 130 itself. According to a software implementation, embodiments such as the procedures and functions described herein may be implemented with separate software modules. Each of the software modules may perform one or more of the functions and operations described herein.

FIG. 12 is a flowchart illustrating an image processing method of an image processing apparatus, according to an example embodiment.

Referring to FIG. 12, the image processing apparatus 100 receives a first image and a second image, at operation S1210. In this regard, the first image and the second image may be images which are generated by photographing the same object at different times, or may be images which are generated by photographing the same object from different directions at the same time.

In this regard, the image processing apparatus 100 may acquire a second image from an image pre-stored in the image processing apparatus 100 and receive a first image from an external server.

Meanwhile, at least one of the first image and the second image may be an image which is acquired through a CT apparatus, an MRI apparatus, an ultrasound imaging apparatus, a PET apparatus, or an X-ray apparatus.

In addition, the image processing apparatus 100 registers the first image based on the second image and acquire transformation information, at operation S1220. In this regard, the transformation information refers to information which regulates a matching relationship between the first image and the second image. In a case of a homogeneous registration, when the acquired transformation information is applied to the first image, the first image is matched with the second image while an image characteristic (shape) of the first shape is maintained. In a case of in-homogeneous registration, when the acquired transformation information is applied to the first image, an image characteristic (shape) of the first image is modified and the first image is completely matched with the second image. In the present disclosure, the homogeneous registration or the in-homogeneous registration may be used.

In addition, the image processing apparatus 100 obtains a first segment image corresponding to an area of an object from the first image, transforms the obtained a first segment image according to the transformation information, and generates a second segment image corresponding to an area of an object of the second image, at operation S1230.

In addition, the image processing apparatus 100 outputs the generated second segment image, at operation S1240. Any method that provides a second segment image to the user may be used for the outputting. For example, the image processing apparatus 100 may transmit a second segment image to a user terminal or display the second segment image through a display included in the image processing apparatus 100.

Meanwhile, the image processing apparatus 100 may generate a first segment image obtained from the first image. In addition, the image processing apparatus 100 may output the generated first segment image together with the second segment image.

In addition, the image processing apparatus 100 may output a comparison result of the generated first segment image and the second segment image. The comparison result may include a change of length, a change of area, a change of thickness and the like, between areas corresponding to each other in the first segment image and the second segment image.

For example, in the case where the subject in the first image and the second image is a bronchus, the first image is an image photographed during inhalation, and the second image is an image photographed during exhalation, the image processing apparatus 100 may compare the first segment image and the second segment image and output information relating to a change of bronchus during inhalation and exhalation.

The information relating to a change of bronchus may be information relating to a change of at least one from among a thickness of a bronchus wall, a cross-sectional area of a bronchus wall, a diameter of a bronchus, a cross-sectional area of a bronchus, a ratio of a diameter of bronchus to a thickness of a bronchus wall, and a ratio of a cross-sectional area of bronchus to a cross-sectional area of a bronchus wall.

Meanwhile, when a second segment image corresponding to an area of the object in the second image is generated, the first image which is used may include a plurality of images which are photographed at different time points. In this case, the image processing apparatus 100 may perform an image registration process with respect to each of the plurality of images photographed at different time points based on the second image and acquire a plurality of transformation information. In addition, the image processing apparatus 100 obtains a segment image corresponding to an area of an object from each of the plurality of images. In addition, the image processing apparatus 100 transforms each of the plurality of obtained segment images according to each of the plurality of transformation information and generate a plurality of transformation images. In addition, the image processing apparatus 100 may output the plurality of generated transformation images together or individually. Alternatively, the image processing apparatus 100 may register the plurality of generated transformation images and generate a second segment image corresponding to an area of the object in the second image.

Meanwhile, methods according various example embodiments may be embodied in software and mounted to the electronic apparatus.

For example, a non-transitory computer readable medium of which stored a program for performing the step of receiving a first image and second image which are generated by photographing the same object at different times, the step of acquiring transformation information by registering the first image based on the second image, the step of generating a second segment image corresponding to an area of the object in the second image by obtaining a first object image corresponding to the object from the first image and transforming the obtained first object image according to the transformation information.

The non-transitory computer readable medium refers to a medium that stores data semi-permanently rather than storing data for a very short time, such as a register, a cache, a memory or etc., and is readable by an apparatus. In detail, the above-described various applications or programs may be stored in the non-transitory computer readable medium, for example, a compact disc (CD), a digital versatile disc (DVD), a hard disc, a Blu-ray disc, a universal serial bus (USB), a memory card, a read only memory (ROM), and the like, and may be provided.

The foregoing exemplary embodiments and advantages are merely exemplary and are not to be construed as limiting the present disclosure. The present teaching may be readily applied to other types of apparatuses. Also, the description of the exemplary embodiments of the present disclosure is intended to be illustrative, and not to limit the scope of the claims, and many alternatives, modifications, and variations will be apparent to those skilled in the art.

What is claimed is:

1. An image processing apparatus, comprising:
an image receiving unit for receiving a first image and a second image of the same object taken at different times;
a processor configured for:
obtaining transformation information by registering the first image on the basis of the second image,
obtaining a first segment image corresponding to an area of the object from the first image, and
generating a second segment image corresponding to an area of the object of the second image by transforming the obtained first segment image according to the transformation information; and
an output unit for outputting the second segment image.

2. The image processing apparatus as claimed in claim 1, wherein the processor is further configured for controlling the output unit to output the first segment image obtained from the first image together with the second segment image.

3. The image processing apparatus as claimed in claim 1, wherein the processor is further configured for controlling the output unit to output a comparison result between the first segment image obtained from the first image and the second segment image.

4. The image processing apparatus as claimed in claim 1,
wherein the object is a bronchus,
wherein the first image is an image taken during inhalation,
wherein the second image is an image taken during exhalation, and wherein the processor is further configured for comparing the first segment image and the second segment image and controls the output unit to output information relating to a change of the bronchus during inhalation and exhalation.

5. The image processing apparatus as claimed in claim 4, wherein the information relating to the change of the bronchus is information relating to a change of at least one of a thickness of a bronchus wall, a cross-sectional area of a bronchus wall, a diameter of a bronchus, a cross-sectional area of a bronchus, a ratio of a diameter of a bronchus to a thickness of a bronchus wall, and a ratio of a cross-sectional area of a bronchus to a cross-sectional area of a bronchus wall.

6. The image processing apparatus as claimed in claim 1, wherein the processor, in response to the first image including a plurality of images of the first image taken at different times, is further configured for:
   obtaining a plurality of first segment image from the plurality of images,
   generating a plurality of transformation images by transforming the plurality of first segment images according to a plurality of transformation information acquired in a registration process of the plurality of images, and
   generating the second segment images by combining the plurality of transformation images.

7. The image processing apparatus as claimed in claim 1, wherein at least one of the first image and the second image is an image which is acquired through a computed tomography (CT) apparatus, a magnetic resonance imaging (MRI) apparatus, an ultrasound imaging apparatus, a positron emission tomography (PET) apparatus, or an X-ray apparatus.

8. The image processing apparatus as claimed in claim 1, wherein the processor is further configured for:
   obtaining the second image from an image pre-stored in the image processing apparatus, and
   receiving the first image from an external server.

9. An image processing method of an image processing apparatus, the method comprising:
   receiving a first image and a second image of the same object taken at different times;
   obtaining transformation information by registering the first image on the basis of the second image;
   generating a second segment image corresponding to an area of the object of the second image by obtaining a first segment image corresponding to an area of the object from the first image and transforming the obtained first segment image according to the transformation information; and
   outputting the second segment image.

10. The image processing method as claimed in claim 9, wherein the outputting of the second segment image comprises the first segment image obtained from the first image together with the second segment image.

11. The image processing method as claimed in claim 9, wherein the outputting of the second segment image comprises outputting a comparison result between the first segment image obtained from the first image and the second segment image.

12. The image processing method as claimed in claim 9, wherein the object is a bronchus,
   wherein the first image is an image taken during inhalation,
   wherein the second image is an image taken during exhalation, and
   wherein the outputting of the second segment image comprises:
      comparing the first segment image and the second segment image, and
      outputting information relating to a change of the bronchus during inhalation and exhalation.

13. The image processing method as claimed in claim 12, wherein the information relating to the change of the bronchus is information relating to a change of at least one of a thickness of a bronchus wall, a cross-sectional area of a bronchus wall, a diameter of a bronchus, a cross-sectional area of a bronchus, a ratio of a diameter of a bronchus to a thickness of a bronchus wall, and a ratio of a cross-sectional area of a bronchus to a cross-sectional area of a bronchus wall.

14. The image processing method as claimed in claim 9, wherein, in response to the first image including a plurality of images of the first image taken at different times, the generating of the second segment image comprises:
   obtaining a plurality of first segment image from the plurality of images,
   generating a plurality of transformation images by transforming the plurality of first segment images according to a plurality of transformation information acquired in a registration process of the plurality of images, and
   generating the second segment images by combining the plurality of transformation images.

15. The image processing method as claimed in claim 9, wherein at least one of the first image and the second image comprises an image which is acquired through a computed tomography (CT) apparatus, a magnetic resonance imaging (MRI) apparatus, an ultrasound imaging apparatus, a positron emission tomography (PET) apparatus, or an X-ray apparatus.

* * * * *